United States Patent [19]

Roche et al.

[11] Patent Number: 5,215,755
[45] Date of Patent: Jun. 1, 1993

[54] ROTOGRANULATIONS AND TASTE MASKING COATINGS FOR PREPARATION OF CHEWABLE PHARMACEUTICAL TABLETS

[75] Inventors: Edward J. Roche, Paoli; Joseph P. Reo, Harleysville, both of Pa.

[73] Assignee: McNeil-PPC, Inc., Milltown, N.J.

[21] Appl. No.: 686,723

[22] Filed: Apr. 17, 1991

Related U.S. Application Data

[63] Continuation-in-part of Ser. No. 389,645, Aug. 4, 1989, abandoned.

[51] Int. Cl.$^5$ .............................................. A61K 9/36
[52] U.S. Cl. ........................... 424/480; 424/441; 424/469; 424/470; 424/474; 424/494; 424/495; 514/974
[58] Field of Search ............... 424/494, 470, 469, 441, 424/474, 495, 480; 514/974

[56] References Cited

U.S. PATENT DOCUMENTS

| | | | |
|---|---|---|---|
| 3,594,470 | 7/1971 | Borodkin | 424/483 |
| 4,800,087 | 1/1989 | Mehta | 424/497 |
| 4,835,187 | 5/1989 | Reuter | 514/570 |
| 4,835,188 | 5/1989 | Ho | 514/570 |
| 4,837,031 | 6/1989 | Denton | 424/464 |
| 4,851,226 | 7/1989 | Julian | 424/441 |

FOREIGN PATENT DOCUMENTS

70177/87 9/1987 Australia.
2166651A 10/1985 United Kingdom.

OTHER PUBLICATIONS

Naji M. Najib et al., "Characteristics of the invitro release of ibuprofen from polyvinylpyrrolidone solid dispersions", pp. 229-236.

*Primary Examiner*—Thurman K. Page
*Assistant Examiner*—D. Gabrielle Phelan

[57] ABSTRACT

Chewable medicament tablets are made from coated rotogranules of a medicament wherein the rotogranules are formed from a granulation mixture of medicament, e.g. ibuprofen, polyvinylpyrrolidone, sodium starch glycolate and sodium lauryl sulfate and the rotogranules are coated with hydroxyethyl cellulose or a mixture of hydroxyethyl cellulose and hydroxypropyl methylcellulose and a process for making such tablets and a method of providing taste masking of medicaments utilizing such coated rotogranules in a tablet.

17 Claims, No Drawings

ROTOGRANULATIONS AND TASTE MASKING COATINGS FOR PREPARATION OF CHEWABLE PHARMACEUTICAL TABLETS

FIELD OF THE INVENTION

This application is a continuation-in-part of U.S. Ser. No. 389,645 filed Aug. 4, 1989, now abandoned.

This invention relates to tablets containing means to mask the taste of active ingredients. More particularly, the taste masking of active ingredients is achieved by rotogranulating active material with binders and ingredients for improving dissolutions and bioavailability of the active granulations and coating such rotogranulations with hydroxyethyl cellulose and hydroxypropyl methylcellulose.

BACKGROUND OF THE INVENTION

Orally administered medicaments are given to the patient in many forms, such as liquid solutions, emulsions, or suspensions, or in solid form such as capsules or tablets (as used herein, the term "tablet" means any shaped and compressed solid dosage form, including caplets). Medicaments administered in tablet or capsule form are usually intended to be swallowed whole. Therefore, the often disagreeable taste of the active ingredient need not be taken into account in formulating the medicine, except for the provision of means to prevent the taste from being apparent during the short time that the medicine is in the mouth. Such means may include the provision of an appropriately thin and quickly dissolving coating on the tablet, the use of the gelatin capsule form (the gelatin outer shell of the capsule keeps the active ingredient inside until the capsule has been swallowed), or simply compressing a tablet firmly so that it will not begin to disintegrate during the short time that it is intended to be in the mouth.

Children, older persons, and many other persons have trouble swallowing whole tablets and even capsules. Therefore, in cases where the dosage to be administered cannot be made into a very small tablet or capsule, it is desirable to provide the medicine either in liquid form or in a chewable solid form, in addition to the tablet or capsule that is designed to be swallowed whole. Even where the medicine can be formulated as a liquid, it is desirable also to be able to provide a chewable solid form because it is usually more convenient to carry a supply of tablets with oneself all day than a container of liquid medicine.

A common problem with chewable tablet forms is the often disagreeable taste of the active ingredient which manifests itself during chewing. In some cases, the taste of the active medicament in a tablet can be overpowered by adding flavoring ingredients to the tablet so that when it is chewed, the taste of the active ingredient is simply overpowered. For instance, this has been done with children's aspirin where the dosage is small enough so that the amount of flavoring agents needed to mask the taste of the medicine is not so great that the tablet becomes unreasonably large. A different approach is taken with a commercially available children's size tablet of acetaminophen (acetyl para-aminophenol or "APAP") wherein the APAP is present in granules that are coated with ethyl cellulose. A significant proportion of the APAP remains shielded by the coating (and therefore does not contribute to taste) while the tablet is in the mouth, despite some breakage of the ethyl cellulose coating during compression of the tablet and some additional breakage of the coating during chewing. The APAP becomes bioavailable via permeation through the coating (although ethyl cellulose is not soluble in aqueous fluids, water does permeate through the coating) and from the granules where the coating is broken.

The present invention is directed to the discovery of a granulating and coating process for active medicaments which can achieve a better balance between taste masking and bioavailability than ethyl cellulose or other previously known coating combinations.

SUMMARY OF THE INVENTION

As embodied and fully described herein, the present invention provides chewable tablets of a medicament comprising compressed coated granules. The coated granules individually comprise a medicament which has been granulated with polyvinylpyrrolidone, sodium starch glycolate and sodium lauryl sulfate and coated with hydroxyethyl cellulose or a mixture of hydroxyethyl cellulose and hydroxypropyl methylcellulose. In preferred embodiments the medicament is provided in a rotogranulation blend of from about 84 to about 96.5% medicament, about 2 to about 10% polyvinylpyrrolidone (PVP), about 1.0 to about 4.0% sodium starch glycolate (SSG) and about 0.5 to about 2.0% sodium lauryl sulfate (SLS) by weight of the weight of the total composition. In further embodiments a coating of hydroxyethyl cellulose (HEC) or a mixture of hydroxyethyl cellulose and hydroxypropyl methylcellulose (HPMC) is added to these rotogranulated particles. The HEC and HEC/HPMC coatings provide excellent taste masking while still permitting acceptable bioavailability of the active ingredient.

In preferred embodiments of the invention, the coated medicament is included in a chewable tablet comprising compressed individual rotogranulated particles of medicament, a binding effective amount of PVP, SSG and effective amounts of SLS to provide adequate bioavailability of the medicament. The rotogranulation medicament is coated with a taste masking effective amount of HEC or HEC/HPMC preferably about 15 to 24% by weight of the total weight of the coated granules.

The ratio of HEC/HPMC is in the range of from 90:10 to 40:60, preferably about 50:50.

In further preferred embodiments, the coated medicament comprises ibuprofen particles rotogranulated with PVP, SSG and SLS and coated with HEC or HEC/HPMC. The coated particles are then compressed into tablet form together with excipients, and flavoring agents to produce chewable tablets.

As embodied and fully described herein, the present invention also provides a granulated composition comprising a medicament, a binder and an amount of sodium lauryl sulfate which is effective to improve dissolution of the granulation composition.

In preferred embodiments the granulation additionally comprises an amount of sodium starch glycolate which is effective to improve bioavailability of the medicament and more preferably the binder is polyvinyl pyrrolidone.

The invention also provides a process of making the rotogranulated particles and methods of using the rotogranulation process to make chewable tablets.

DESCRIPTION OF THE INVENTION

The invention will now be described specifically in terms of its most preferred embodiments which are the preparation of rotogranulations of ibuprofen and chewable tablets comprising coated rotogranules of ibuprofen. Ibuprofen is a medicament used in both over-the-counter preparations and in prescription drugs for analgesic and antipyretic purposes. Uncoated ibuprofen has a bitter soapy taste and also may impart irritation or burning in the throat absent its proper barrier separation or masking from the mouth and throat. Reference will also be made in detail herein to other preferred embodiments of the compositions, processes and methods of the invention.

In accordance with preferred embodiments of the invention medicament powders, preferably raw ibuprofen, PVP, SSG and SLS are rotogranulated with water to produce nearly spherical granulated particles. These particles are preferably in the size range of 40 to 80 mesh (U.S. Sieve Series), i.e. the particles are of a size (177 to 420 microns) that will pass through a 40 and are retained by an 80 mesh sieve screen.

The rotogranulation is formed by blending about 84 to 96.5% by weight raw ibuprofen with about 2 to 10% by weight PVP, about 1.0 to about 4.0% SSG and about 0.5 to 2% by weight SLS. Percentages by weight herein are weight by weight of the total composition. These weight percentages relate most directly to ibuprofen granulations, but generally apply to other useful medicaments including, for example, naproxen, pseudoephedrine, dextromethorphan, chlorpheniramine, loperamide, their pharmaceutically acceptable salts and combinations thereof. These amounts may vary for particular applications, especially with lower dose active ingredients such as loperamide as would be known to those skilled in the art.

Details of a preferred process of rotogranulating and subsequent fluid-bed coating are provided in the examples section. Preferred methods are further described in: Jones, D. M. "Factors to Consider in Fluid-bed Processing," *Pharmaceutical Technology*, April, 1985, Pg. 50-63; and Jager, K. F. et al., "Effect of Material Motion on Agglomeration in the Rotary Fluidized-Bed Granulator," *Drugs Made in Germany*, Vol. XXV, Pg. 61-65 (1982). The entire disclosure of these articles are hereby incorporated herein by reference. Granules of ibuprofen produced by rotogranulation in accordance with the invention are nearly spherical in shape and will be referred to hereinafter as "rotogranules".

Rotogranules have increased strength due to the compaction or densification of the granulation mixture as rotogranules are formed by rotation in the rotogranulator bed. The ibuprofen rotogranules have excellent integrity and enough strength to withstand fluid bed coating processes without significant breakage. This resistance to breakage is advantageous since broken particles which are of a smaller size than the rotogranules are not easily coated in subsequent coating steps. Smaller sized particles without proper coating detracts from the taste masking purpose of the coating by providing a poor taste to the mixture as a whole. Further, smaller sized particles tend to agglomerate and interfere with subsequent fluid bed coating.

PVP or povidone acts as a binder in the granulation process. Use of PVP as a binder imparts good mechanical strength to the granules. In this respect PVP is superior to other binders such as cellulosic polymers, e.g. methylcellulose, or starch. Sodium starch glycolate (SSG) is a disintegrant which provides superior bioavailability of the medicament in the granulations of the invention. Other useful disintegrants may include other starches, croscarmellose sodium or crospovidone.

Sodium lauryl sulfate (SLS) is a surfactant which aids in the wetting of the granules in the body, increasing the release rate of ibuprofen or other water insoluble medicaments. SLS is a surfactant with a very high HLB (hydrophilic-lipophilic balance) number and its use obtains good wetting and rapid dissolution of the medicament granulation of the invention. Other useful surfactants may include potassium and sodium oleates.

In preferred embodiments of the compositions and processes of the invention, medicament, preferably ibuprofen in rotogranular form, is coated with HEC polymer or preferably a blend of HEC/HPMC polymer. The coated granules, together with other ingredients such as flavoring agents, extenders, excipients, and the like, are compressed into tablet form. (As used herein, the term "granule" refers to individual rotogranulated particles or to agglomerates of individual particles of the medicament.)

Ibuprofen has a relatively slow intrinsic dissolution rate particularly at acid pH conditions such as in the stomach. Coating of ibuprofen with non-water soluble polymers such as cellulose acetate produces particles that do not release the ibuprofen rapidly enough for an on-demand antipyretic/analgesic product. The HEC polymer used in the present invention is a water soluble polymer which effects rapid release of ibuprofen and other medicaments. The HEC polymer also has good mechanical flexibility which is advantageous in a product where the coating must withstand the forces of tablet compression and chewing in the mouth. HPMC is a water dispersible polymer which reduces tackiness of the coating and toughens the film coating when blended with HEC in weight to weight ratios of up to 60% HPMC and 40% HEC, preferably about a 50/50 blend. Blends of HEC/HPMC will disintegrate rapidly to provide rapid release of the medicament upon swallowing and maintain good bioavailability.

A high enough proportion of HEC or HEC/HPMC coating remains effectively intact on the ibuprofen granules through the compression of the tablet and through normal chewing in the mouth to permit effective taste masking of the normally bitter tasting ibuprofen. The term "effectively intact" means that the coating remains sufficiently integral to mask the taste or flavor of the medicament. This taste masking is effective to mask the unpleasant flavor of the medicament without requiring large and bulky amounts of overpowering flavoring agents. When the coated granules are swallowed, the active medicament becomes bioavailable via permeation as the coating disintegrates. Permeation can occur through the intact coating but is encouraged by the disintegration of the coating which becomes porous through dissolution of the water soluble HEC and water dispersible or soluble HPMC.

Other additives which are preferably water soluble may be added to reduce the tackiness and/or toughen the film coating. Such additives may include, for example, a copolymer of polyethylene glycol and polypropylene glycol at an add-on of about 10 to 30% by weight of the total weight of the coated medicament.

The coated rotogranules may be made by coating with an aqueous solution of HEC polymer or HEC/HPMC polymer blend in a fluidized bed coating operation. The HEC or HEC/HPMC polymer is dissolved in water and the polymer solution is then coated onto ibuprofen or other rotogranules of active medicament ingredient or combination of ingredients, using a fluidized bed coater. Air (which may be heated) passes through a bed of the medicament granules to fluidize them, and the solvent solution of the polymer is sprayed onto the fluidized bed and thereby coats the granules. The air passing through the bed dries the coated granules, so that a dry coated granule is obtained. The coated granules are then used in combination with various excipients, flavors, and colors to make a chewable tablet.

As a general rule, the proportion of polymer in the solvent solution will be from about 5 to 14 and preferably 5 to 10 weight percent, depending upon the process parameters. As a practical matter, a concentration of less than 5% HEC or HEC/HPMC would unduly lengthen the coating process and a concentration of more than 14% HEC or HEC/HPMC would hamper spraying of the thickened solution. The coating level of HEC or HEC/HPMC is in the range of about 12 to 26% and preferably about 15 to 24% by weight of the total coated composition to achieve optimal taste masking and bulk characteristics. The coating solution in addition to film toughening agents may include agents to reduce tackiness such as kaolin or magnesium oxide.

The exact proportions of coating to medicament desired for individual cases can be determined by routine experimentation. The amount of coating may be varied in light of the intended application and desired bulk of the products. Chewable tablets can be acceptable in larger sizes than swallowed tablets since chewing will reduce the size of the material to be swallowed. Further, tablets intended for pediatric use generally comprise reduced dosage amounts and less bulk. Larger proportions of coating may be used to provide a better tasting formulation.

While exact size of the coated granules has not been found to be critical, the coated granules, preferably are sized so that the majority will pass through a 20 and are retained by an 80 mesh sieve screen (hereinafter all "mesh" size refers to U.S. Sieve Series).

In addition to ibuprofen, other solid medications in need of taste masking can be used in the invention.

Illustrative embodiments include naproxen, pseudoephedrine, dextromethorphan, chlorpheniramine, loperamide and combinations thereof. Identification of medicaments herein is intended to apply to pharmaceutically acceptable salts thereof as well. Further, the coating of the invention provides a convenient means for providing a viable dosage form for combination medicaments which are incompatible before (e.g. during storage) or after administration. For example, combinations of ibuprofen and pseudoephedrine, chlorpheniramine maleate or other ingredients such as pyrilamine maleate.

An illustrative preferred procedure for coating the rotogranules of medicament in accordance with the invention is briefly described here and provided in more detail in the following examples section. The medicament, in rotogranular form, is preferably placed in a fluidized bed coater and is fluidized by a flow of warm air. The temperature of the air has not been found to be narrowly critical, and can vary over a wide range, keeping in mind the fact that the temperature should not be high enough to cause decomposition, sintering, or melting of the medicament granules. When coating ibuprofen rotogranules, a temperature of from about 35° and 55° C. is maintained. The rate of air flow is adjusted so as to fluidize the granules. Such flow will vary depending on factors such as the specific equipment used, the size of the charge of granules, the size of the individual granules, the apparent specific gravity of the granules, and other factors that are known to those skilled in the art of fluidized bed coating.

After the medicament has been fluidized, the polymer solution is sprayed via bottom, top or tangential spray onto the fluidized bed. The air flow through the bed is continued until the amount of solvent remaining in the coating has been greatly reduced. The granules are actually dry to the touch within a very short time after the coating solution has been sprayed onto the granules of medicament; a matter of a few seconds in some cases. The total drying time required to ensure that the solvent content of the coating has been reduced to the level desired may take much longer, depending on the temperature of the air, the size of the batch, and the like. Since the present invention utilizes water as the solvent dryness is not as critical a parameter as it would be for organic solvent systems. Routine experimentation will suffice to determine the appropriate air temperatures and total times required in the fluidized bed coaters in individual cases.

While the use of fluidized bed coating has been described in some detail as the preferred method for making the coated granules that are utilized in the invention, other techniques for making the coated granules may be used. Such other techniques include various microencapsulation techniques such as coacervation, solvent evaporation and rotogranulation.

The invention will now be illustrated by examples. The examples are not intended to be limiting of the scope of the present invention but read in conjunction with the detailed and general description above, provide further understanding of the present invention and an outline of a process for preparing the rotogranular compositions and chewable medicament tablets of the invention.

EXAMPLES

The Examples below set forth the ingredients and proportions for typical laboratory scale preparations of coated medicament granules. The materials used are the following:

Ibuprofen—in the form of powders having a particle size less than 40 microns;

Loperamide (HCl salt)—in the form of powder having a particle size of about 40–80 mesh;

Pseudoephedrine hydrochloride—in the form of powder having a size less than 40 microns.

PVP—in the form of a white powder.

SSG—in the form of a white powder.

SLS—in the form of a white powder.

HEC—in the form of a white free flowing fine powder.

HPMC—in the form of a white powder.

The coating methods used are disclosed for example in Jones, D. M. "Factors to Consider in Fluid-Bed Processing" *Pharmaceutical Technology*, April, 1985 and Rotogranulating methods are taught by, for example, in Jager, K. F. et al., "Effect of Material Motion on Agglomeration in the Rotary Fluidized-Bed Granulator", *Drugs Made in Germany*, Vol. XXV, Pp. 61–65 (1982) which have been incorporated herein by reference. The term "total coat" refers to the proportion of coating to medicament in the coated granule product, "charge" to the weight of medicament, "polymer solution" to the proportion of polymer in the aqueous solution, and "total batch" to the weight of medicament plus coating.

EXAMPLE I

Rotogranulation/Coating of Ibuprofen

Rotogranulation: Charge 5000 gms. of ibuprofen, 210.5 gms. of PVP and 52.6 gms. of SLS into a rotary fluidized-bed granulator. Set supply air temperature at 40° to 50° C. Spray 1900 mg of purified water at 75 gm/min while rotating batch at 500 RPM. After spraying, dry batch by heating supply air above 40° C. but not to exceed 50° C., decrease rotation speed to 250 RPM. Continue drying until exhaust air reaches 30°-32° C.

Coating: Prepare coating solution by weighing 400 gms of HEC and 400 gms of HPMC and 9200 gms of purified water (8% solution) into a suitable container. Stir vigorously to obtain a clear solution having a viscosity of between 150-400 centipoise at 25° C. Load rotogranulated ibuprofen into a Glatt Wurster brand Fluid Bed coating insert. Fluidize product. Spray coating solution using a bottom spray technique. Adjust spray rate to maintain a product temperature of 35°-40° C. After spraying 9600 gm of HEC/HPMC solution continue to fluidize product until product temperature reaches 42°-44° C. Pass coated product through a 14 mesh screen. The coating level attained is about 18% by weight.

EXAMPLE II

Rotogranulation/Coating of Ibuprofen

Rotogranulation: Charge 5000 gms. of ibuprofen and 52.6 gms. of SLS into a rotary fluidized-bed granulator. Prepare granulating solution by mixing 210.5 gms. of PVP into 1900 gms. of purified water. Spray granulating solution while rotating batch as in Example I. Proceed to dry batch and carry out coating as described above in Example I.

EXAMPLE III

Rotogranulation/Coating of Ibuprofen

Rotogranulation: Carry out as in Example I. Coating: Prepare coating solution as in Example 1. Spray coating solution using tangential spray mode in rotogranulation unit. Dry batch in rotogranulation unit.

EXAMPLE IV

Rotogranulation of Pseudoephedrine

Rotogranulation: Charge 5000 gms. of pseudoephedrine hydrochloride and 210.5 gms of PVP into rotogranulation unit. Spray purified water while rotating batch. After spraying continue to rotate batch at reduced RPM to dry. Coating: Carry out coating as in Example I.

Examples V-VIII, below, display the identity of medicament(s), coating polymers, solvent and solutions of coating polymers, and the proportions of all of these materials for typical laboratory scale batches of coated medicament granules for use in the invention in accordance with the preferred procedure for preparing coated granules of medicament as described above for Example I-IV. The polymer blend in Example V is 360/90 gram of HEC/HPMC blend, i.e. 80/20. The HEC/HPMC polymer is a 50/50 blend in Examples VI-VIII.

EXAMPLE V

|  | Amount |
| --- | --- |
| Total Coat 10% w/w Charge of ibuprofen | 4050 gms |
| Total HEC/HPMC Polymer in 10% Aqueous Polymer Solution | 450 gms |
| Total Dry Batch | 4500 gms |

EXAMPLE VI

| Total Coat 15% w/w Charge of naproxen | 4000 gms |
| --- | --- |
| Total HEC/HPMC Polymer blend in 10% Aqueous Polymer Solution | 355/350 or 705 gms |
| Total Dry Batch | 4705 gms |

EXAMPLE VII

|  | Amount |
| --- | --- |
| Total Coat 12% w/w |  |
| Charge ibuprofen | 3520 gms |
| pseudoephedrine hydrochloride | 480 gms |
| Total HEC/HPMC Polymer blend in 10% Aqueous Polymer Solution | 545.45 gms |
| Total Dry Batch | 4545.45 gms |

EXAMPLE VIII

| Total Coat 12% w/w Charge loperamide HCl | 4000 gms |
| --- | --- |
| Total HEC/HPMC Polymer blend in 10% Aqueous Polymer Solution | 545.45 gms |
| Total Dry Batch | 4545.45 gms |

The following examples IX and X describe preparation of pediatric chewable tablets.

The functions of several ingredients utilized in examples IX and X and some typical replacements for them are as follows:

Mannitol is a sweetener which can be replaced by dextrose, fructose, sorbitol, compressible sugar, and/or lactose;

Microcrystalline cellulose is used as a binder, and can be replaced with other binders such as alginic acid, carboxymethyl cellulose, hydroxypropylmethylcellulose, PVP, or starch;

Aspartame is an artificial sweetener which can be replaced with others such as saccharin;

Magnesium stearate is a lubricant (to lubricate the dye walls and punches used during the tablet compression procedure). It can be replaced by talc, stearic acid, calcium stearate, zinc stearate, leucine, glycerides, sodium stearyl fumarate or the like;

Citric acid is used as an acidifying agent to enhance the taste and can be replaced by other acidifying agents such as malic acid; and Artificial and natural flavor agents can be any conventional artificial and natural flavoring agents and flavor enhancers such as vanilla, grape, peppermint, orange, cherry, and/or spearmint flavors and conventional flavor enhancers or sweeteners.

EXAMPLE IX AND X

PREPARATION OF CHEWABLE TABLETS

The ingredients displayed below for Examples IX and X, were sieved, dry blended, and compressed by standard procedures into round (disc shaped) chewable tablets, each weighing 485.91 mg. (Ex. IX) and 607.41 mg. (Ex. X). Each tablet of Example IX contained 40 mg. and Example X contained 50 mg. of active ibuprofen per tablet from coated granules prepared in accordance with the procedure of Example 1 containing 18 weight percent HEC/HPMC coating.

EXAMPLE IX

| Component | mg/Tablet |
| --- | --- |
| Ibuprofen, USP | 40.00 |
| Povidone USP (K29-32) | 1.69 |
| Sodium Lauryl Sulfate NF | 0.42 |
| Hydroxyethyl cellulose NF (NATROSOL 250L) | 4.62 |
| Hydroxypropyl methylcellulose NF (METHOCEL E5) | 4.62 |
| Mannitol (Granular) USP | 380.00 |
| Microcrystalline Cellulose NF | 32.00 |
| Citric Acid USP Anhydrous Powder | 3.14 |
| Aspartame NF | 7.48 |
| Artificial and Natural Flavors | 7.68 |
| FD & C Red No. 7 Color | 0.65 |
| FD & C Blue No. 1 Color | 0.33 |
| Magnesium Stearate NF | 3.28 |
| Total | 485.91 mg |

EXAMPLE X

| Ingredients | mg per tablet |
| --- | --- |
| Ibuprofen, USP | 50.00 |
| Povidone USP (K29-32) | 2.11 |
| Sodium Lauryl Sulfate NF | 0.53 |
| Hydroxyethyl cellulose NF (NATROSOL TM 250L) | 5.78 |
| Hydroxypropyl methylcellulose NF (METHOCEL TM E5) | 5.78 |
| Mannitol (Granular) USP | 280.53 |
| Microcrystalline Cellulose NF | 23.62 |
| Citric Acid USP Anhydrous Powder | 2.32 |
| Aspartame NF | 5.52 |
| Artificial and Natural Flavors | 5.68 |
| 7 Coloring | 0.73 |
| Magnesium Stearate NF | 2.42 |
| Total | 385.02 mg. |

EXAMPLE XI

In order to demonstrate the extent of bioavailability (as evidenced by dissolution rates) that is obtained with HEC/HPMC coating on rotogranules of medicament, i.e. ibuprofen, times of dissolution at pH 5.6 (900 cc potassium phosphate buffer) in a USP Apparatus (II) at 50 RPM were obtained for uncoated rotogranules of ibuprofen and rotogranules of ibuprofen coated with 18% HEC/HPMC by weight of the total weight of the granules as prepared in accordance with the method of Example I. The results are provided below:

| Rotogranules | Dissolution at: | | |
| --- | --- | --- | --- |
| | 5 minutes | 10 minutes | 30 minutes |
| Uncoated rotogranules of ibuprofen (Ex. I) | 34% | 94% | 100% |
| Rotogranules of ibuprofen coated with 18% HEC/HPMC (Ex. I) | 20% | 91% | 100% |

EXAMPLES DEMONSTRATING IMPROVED DISSOLUTION AND BIOAVAILABILITY

The following examples illustrate preferred embodiments of the compositions including granulations and chewable tablets of the invention which utilize a disintegrant, i.e., sodium starch glycolate (SSG) in the medicament granulation mixture to improve bioavailability of the medicament.

Examples XII and XIII prepared in accordance with the rotogranulation procedure of Example I illustrate the importance of the presence of SLS to achieve good dissolution results:

| Formula (% W/W): | XII | XIII |
| --- | --- | --- |
| Ibuprofen | 93 | 94 |
| Povidone K 29-32 (PVP) | 4 | 4 |
| Sodium starch glycolate (SSG) | 2 | 2 |
| Sodium lauryl sulfate (SLS) | 1 | 0 |
| Purified Water | qs | qs |

TABLE 1

Dissolution results (mean percent dissolved) carried out in a pH 5.6 potassium phosphate buffer:

| Time (min) | XII | XIII |
| --- | --- | --- |
| 0 | 0 | 0 |
| 1 | 31.0 | 15.0 |
| 2 | 50.4 | 16.4 |
| 3 | 66.6 | 23.9 |
| 4 | 74.2 | 27.9 |
| 5 | 84.9 | 32.4 |
| 10 | 91.5 | 39.2 |
| 15 | 93 | 56.7 |

The above demonstrates clearly superior dissolution results of the granulation which includes SLS in an amount effective to improve dissolution of the granulation.

Examples XIV is a chewable tablet comprising 50 mg of ibuprofen per tablet and is prepared substantially in accordance with the procedures of Examples I and X except that 1.08 mg of sodium starch glycolate (SSG) is added to the granulation mixture and included in the tablet. The formulation for Example XIV is as follows:

| | |
| --- | --- |
| Ibuprofen, USP | 50.00 |
| Povidone USP (K29-32) | 2.15 |
| Sodium Lauryl Sulfate NF | 0.54 |
| Sodium Starch Glycolate NF Explotab® | 1.08 |
| Hydroxyethylcellulose NF (NATROSOL® 250L) | 5.90 |
| Hydroxypropylmethyl-cellulose (METHOCEL® E5) | 5.90 |
| Mannitol (Granular) USP | 264.03 |
| Microcrystalline Cellulose NF | 42.07 |
| Citric Acid Anhydrous Powder | 2.13 |

-continued

| | |
|---|---|
| Aspartame NF | 5.41 |
| Flavoring | 2.15 |
| Coloring | 0.88 |
| Magnesium Stearate NF | 2.76 |
| TOTAL | 385.00 |

The bioavailability of Example X (without SSG) and Example XIV is demonstrated by the following tables. The tables are average plasma ibuprofen levels for six subjects treated with four tablets of Example X and an average plasma ibuprofen level for twenty-five subjects treated with four tablets of Example XIV. Both studies used a total 200 mg ibuprofen dose, and all of the subjects fasted for 12 hours prior to administration. The results are shown in Table II below:

TABLE II

| Plasma ibuprofen levels (ug/mL) after treatment A: with four 50 mg tablets of Examples X and IV: | | | | | | | | |
|---|---|---|---|---|---|---|---|---|
| Time post dosing (hr.) | | | | | | | | |
| 0.0 | 0.50 | 1.0 | 1.5 | 2.0 | 2.5 | 3.0 | 4.0 | 6.0 |
| Example X- 6 subjects |||||||||
| 0.00 | 7.32 | 8.90 | 10.08 | 11.51 | 11.62 | 11.27 | 9.13 | 4.01 |
| Example XIV- 25 subjects |||||||||
| 0.00 | 6.93 | 11.34 | 12.92 | 13.34 | 12.55 | 11.45 | 8.50 | 4.00 |

Table II illustrates the superior bioavailability achieved particularly over 1 to 3 hours for the medicament (ibuprofen) in chewable tablets of Example XIV containing SSG in the granulation. The amount of SSG included is effective to enhance the bioavailability of the medicament as demonstrated by a comparison of the average plasma ibuprofen levels for tablets without SSG (Example X) vs. those tablets with SSG (Example XIV) as reported therein.

The scope of the present invention is not limited by the description, examples and suggested used herein and modifications can be made without departing from the spirit of the invention. For example, other components may be added to the tablets including additional actives, various flavorings, preservatives and other pharmaceutical excipients. The present invention may also be used to provide a chewable form for vitamins, minerals or other nutrients.

Application of the compositions and processes of the present invention for medical and pharmaceutical uses can be accomplished by any clinical, medical and pharmaceutical methods and techniques as are presently and prospectively known to those skilled in the art. Thus it is intended that the present invention cover the modifications and variations of this invention provided that they come within the scope of the appended claims and their equivalents.

We claim:

1. A chewable tablet of a medicament comprising compressed coated granules, said coated granules individually consisting essentially of a granule containing a medicament provided in the range of from about 84 to about 96.5 percent by weight which has been granulated with polyvinylpyrrolidone provided in the range of from about 2 to about 10 percent by weight, sodium starch glycolate provided in the range of from about 1.0 to about 4 percent by weight and sodium lauryl sulfate provided in the range of from about 0.5 to about 2.0 percent by weight, wherein the percents by weight are based on the total weight of the granule, and coated with a coating material selected from the group consisting of hydroxyethyl cellulose and a mixture of hydroxyethyl cellulose and hydroxypropyl methylcellulose wherein said coating is provided in an amount effective to remain effectively intact through normal chewing in the mouth.

2. The chewable tablet of claim 1 wherein the medicament is selected from the group consisting of ibuprofen, naproxen, pseudoephedrine hydrochloride, dextromethorphan, chlorpheniramine, loperamide, and combinations thereof.

3. The chewable tablet of claim 1 wherein the coating mixture has a weight ratio in the range of from 90:10 to 40:60 of hydroxyethyl cellulose to hydroxypropyl methylcellulose.

4. The chewable tablet of claim 1 wherein the hydroxyethylcellulose comprises from about 15 to 24% by weight of the total weight of the coated granules.

5. The chewable tablet of claim 1 wherein the coated granules are substantially spherical in shape.

6. The chewable tablet of claim 1 wherein the medicament comprises ibuprofen.

7. The chewable tablet of claim 1 wherein the medicament comprises loperamide.

8. The chewable tablet of claim 1 wherein the medicament comprises a combination of ibuprofen with a medicament selected from the group consisting of pseudoephedrine hydrochloride, dextromethorphan, chlorpheniramine and mixtures thereof.

9. The chewable tablet of claim 1 wherein in addition to the coated granules in said tablet there are one or more excipients selected from the group consisting of sweeteners, binders, artificial sweeteners, lubricants and acidifying agents, and optionally artificial and natural flavors.

10. The chewable tablet of claim 1 wherein the chewable tablet contains in addition to said coated granules one or more of the excipients selected from the group consisting of:
   a. an effective amount of a sweetener selected from the group consisting of mannitol, dextrose, fructose, sorbitol, compressible sugar and lactose;
   b. an effective amount of a binder selected from the group consisting of microcrystalline cellulose, alginic acid, carboxymethyl cellulose and hydroxypropyl cellulose;
   c. an effective amount of an artificial sweetener selected from the group consisting of asparatame and saccharin;
   d. an effective amount of a lubricant selected from the group consisting of magnesium stearate, talc, stearic acid, calcium stearate zinc stearate, leucine, glycerides and sodium stearyl fumarate; and
   e. an effective amount of an acidifying agent selected from the group consisting of citric acid and malic acid;

and optionally an effective amount of flavoring agent selected from the group consisting of artificial and natural flavors.

11. The chewable tablet of claim 10 wherein;
   a. the medicament is ibuprofen;
   b. the polyvinylpyrrolidone is Povidone K 29-32;
   c. the sweetener is mannitol;
   d. the binder is microcrystalline cellulose;

e. the acidifying agent is citric acid in the form of an anhydrous powder;
f. the artificial sweetener is aspartame; and
g. the lubricant is magnesium stearate.

12. A process of preparing a chewable medicament tablet consisting essentially of:
   rotogranulating a medicament provided in the range of from about 84 to about 96.5 percent by weight with polyvinylpyrrolidone provided in the range of from about 2 to about 10 percent by weight, sodium starch glycolate provided in the range of from about 1.0 to about 4 percent by weight and sodium lauryl sulfate provided in the range of from about 0.5 to about 2.0 percent by weight to form a medicament rotogranulation composition;
   coating the medicament rotogranulation composition with a coating material selected from the group consisting of hydroxyethyl cellulose and a mixture of hydroxyethyl cellulose and hydroxypropyl methylcellulose wherein said coating is provided in an amount effective to remain effectively intact through normal chewing in the mouth thereby forming a coated medicament rotogranulation composition; and
   forming a chewable tablet by compressing the coated medicament rotogranulation composition in the presence of pharmaceutically acceptable excipients.

13. The process of claim 12 wherein the coating mixture has a weight ratio in the range of 90:10 to 40:60 of hydroxyethyl cellulose to hydroxypropyl methylcellulose.

14. The process of claim 13 wherein the coating mixture weight ratio is 50:50.

15. A method of taste masking medicaments consisting essentially of rotogranulating a medicament provided in the range of from about 84 to about 96.5 percent by weight with polyvinylpyrrolidone provided in the range of from about 2 to about 10 percent by weight, sodium starch glycolate provided in the range of from about 2 to about 10 percent by weight and sodium lauryl sulfate provided in the range of from about 0.5 to about 2.0 percent by weight to form a rotogranulated medicament composition wherein the percent by weight is based on the total weight of the granule and coating the rotogranulated medicament composition with a taste masking effective amount of a coating material selected from the group consisting of hydroxyethyl cellulose and a mixture of hydroxyethyl cellulose and hydroxypropyl methycellulose.

16. The method of claim 15 wherein the medicament coated is selected from the group consisting of ibuprofen, naproxen, loperamide, pseudoephedrine hydrochloride, dextromethorphan, chlorpheniramine, and mixtures thereof.

17. The method of claim 15 wherein the medicament is ibuprofen.

* * * * *